(12) United States Patent
Koyama et al.

(10) Patent No.: US 8,669,045 B2
(45) Date of Patent: Mar. 11, 2014

(54) METHOD FOR INACTIVATING VIRUSES WITH SLIGHTLY ACIDIC ARGININE

(75) Inventors: Hajime Koyama, Wakayama (JP); Tsutomu Arakawa, Thousand Oaks, CA (US); Daisuke Ejima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 565 days.

(21) Appl. No.: 12/030,321

(22) Filed: Feb. 13, 2008

(65) Prior Publication Data

US 2008/0318300 A1    Dec. 25, 2008

Related U.S. Application Data

(60) Provisional application No. 60/889,554, filed on Feb. 13, 2007, provisional application No. 60/991,831, filed on Dec. 3, 2007.

(51) Int. Cl.
*C12Q 1/70* (2006.01)

(52) U.S. Cl.
USPC ............................................................ 435/5

(58) Field of Classification Search
None
See application file for complete search history.

(56) References Cited

U.S. PATENT DOCUMENTS

| | | | |
|---|---|---|---|
| 5,110,600 A | 5/1992 | Green | |
| 2003/0087827 A1 | 5/2003 | Lindberg et al. | |
| 2004/0022792 A1* | 2/2004 | Klinke et al. | 424/178.1 |
| 2005/0176109 A1 | 8/2005 | Yumioka et al. | |
| 2006/0199948 A1 | 9/2006 | Ejima et al. | |
| 2007/0004014 A1 | 1/2007 | Tsuji et al. | |
| 2008/0064860 A1* | 3/2008 | Sun et al. | 530/413 |

FOREIGN PATENT DOCUMENTS

WO    WO2007/016450    2/2007

OTHER PUBLICATIONS

Soffer, et al. Virus Inactivation in the 1990s and into the 21st Century: Part 6, Inactivation Methods Grouped by Virus. BioPharm International. 42-68. 2003.*
Boschetti, et al. Different susceptibility of B19 virus and mice minute virus to low pH treatment. Transfusion. 2004; 44(7):1079-1086.*
Sugimoto and Toyoshima Nα-Cocoyl-L-Arginine Ethyl Ester, DL-Pyroglutamic Acid Salt, as an Inactivator of Hepatitis B Surface Antigen. Antimicrobial Agents and Chemotherapy, 1979; 16(3): 329-332.*
Brorson, K., et al., "Bracketed Generic Inactivation of Rodent Retroviruses by Low pH Treatment for Monoclonal Antibodies and Recombinant Proteins," Biotechnol. Bioeng. 2003;82:321-329.
Burstyn, D. G., et al., "Strategies for Viral Removal and Inactivation," Developments in Biological Standardization 1996;88:73-79.
ICH Harmonized Tripartite Guideline: Viral Safety Evaluation of Biotechnology Products Derived from Cell Lines of Human or Animal Origin (step 4), International Conference on Harmonisation of Technical Requirements for Registration of Pharmaceuticals for Human Use, Sep. 23, 1999, pp. 1-27.
Johnston, A., et al., "Low pH, caprylate incubation as a second viral inactivation step in the manufacture of albumin," Biologicals 2003;31:213-221.
Kempf, C., et al., "Virus inactivation during production of intravenous immunoglobulin," Transfusion 1991;31:423-427.
Koyama, A. H., et al., "The Mode of Entry of Herpes Simplex Virus Type 1 into Vero Cells," Microbiol. Immunol. 1987;31(2):123-130.
Koyama, A. H., et al., "The effect of ammonium chloride on the multiplication of herpes simplex virus type 1 in Vero cells," Virus Res. 1989;13:271-282.
Kurokawa, M., et al., "Influenza virus overcomes apoptosis by rapid multiplication," Internat. J. Mol. Med. 1999;3:527-530.
Louie, R. E., et al., "Inactivation of Hepatitis C Virus in Low pH Intravenous Immunoglobulin," Biologicals 1994;22:13-19.
Omar, A., et al., "Virus inactivation by pepsin treatment at pH 4 of IgG solutions: factors affecting the rate of virus inactivation," Transfusion 1996;36:866-872.
Paborji, M., et al., "Chemical and Physical Stability of Chimeric L6, a Mouse-Human Monoclonal Antibody," Pharm. Res. 1994;11(5):764-771.
Sofer, G., "Virus Inactivation in the 1990s—and into the $21^{st}$ Century, Part 3b, Plasma and Plasma Products (Treatment Other than Heat or Solvent/Detergent)," BioPharm Internat., Oct. 2002, pp. 42-51.
Sofer, G., et al., "Virus Inactivation in the 1990s—and into the $21^{st}$ Century, Part 6, Inactivation Methods Grouped by Virus," BioPharm Internat., Apr. 2003, pp. 42-68.
Tsumoto, K., et al., "Role of Arginine in Protein Refolding, Solubilization, and Purification," Biotechnol. Prog. 2004;20:1301-1308.
Cabrera, C., et al., "Anti-Human Immunodeficiency Virus Activity of Novel Aminoglycoside-Arginine Conjugates at Early Stages of Infection," Aids Res. Human Retroviruses 2000;16(7):627-634.
Docherty, J. J., et al., "Inactivation of Herpes Simplex Virus Types 1 and 2 by Synthetic Histidine Peptides," Antimicro. Agents Chemother. 1987;31(10):1562-1566.

(Continued)

*Primary Examiner* — Jeffrey Stucker
*Assistant Examiner* — Stuart W Snyder
(74) *Attorney, Agent, or Firm* — Shelly Guest Cermak; Cermak Nakajima LLP

(57) ABSTRACT

The present invention provides a method for conveniently producing a protein formulation in which viruses are inactivated, without impairing the quality of the obtained protein formulation, characterized by including the step of exposing the protein formulation contaminated with the viruses to a 0.1-2M aqueous solution of arginine, an arginine derivative, or a mixture thereof, the aqueous solution being adjusted to pH 3.5 to 5. The present invention also provides a virus inactivation method characterized by including the step of contacting a virus-containing object with a 0.1-2M aqueous solution of arginine, an arginine derivative, or a mixture thereof, the aqueous solution being adjusted to pH 3.5 to 5.

10 Claims, No Drawings

(56) References Cited

OTHER PUBLICATIONS

Kozloff, L. M., et al., "Critical Arginine Residue for Maintaining the Bacteriophage Tail Structure," J. Virol. 1969;3(2):217-227.
European Search Report for EP Patent App. No. 08250527.2 (Jun. 6, 2008).
Notification of Reason for Rejection for Japanese Patent App. No. 2008-032062 (Nov. 12, 2012) with English translation thereof.
Office Action from Japanese Patent App. No. 2008-032062 (Sep. 9, 2013) with English translation thereof.
Notification of Reason for Rejection for Japanese Patent App. No. 2008-032062 (Dec. 2, 2013) with English translation thereof.

* cited by examiner

METHOD FOR INACTIVATING VIRUSES WITH SLIGHTLY ACIDIC ARGININE

This application claims priority under 35 U.S.C. §119(a) to U.S. Provisional Patent Application No. 60/889,554, filed Feb. 13, 2007, and U.S. Provisional Patent Application No. 60/991,831, Filed Dec. 3, 2007, the entireties of which are incorporated by reference.

BACKGROUND OF THE INVENTION

1. Field of the Invention

The present invention relates to a method for inactivating viruses, which is necessary for the preparation of protein formulations. The method involves adding arginine to a protein formulation at a more moderate pH than acid pH treatments used in convention methods for virus inactivation.

2. Brief Description of the Related Art

During the manufacture of protein formulations, contamination by viruses may occur. Therefore, it is absolutely necessary to provide a step in the manufacturing process of inactivating and/or eliminating viruses (ICH Harmonized Tripartite Guideline: Viral Safety Evaluation of Biotechnology Products Derived from Cell lines of Human or Animal Origin).

A plurality of treatments based on different mechanisms has been conventionally employed to inactivate viruses. These treatments include, for example, pasteurization with continuous heat (about 60° C.) for about ten hours, exposing the protein formulation to a solvent/detergent (S/D) designed for virus inactivation, such as an organic solvent such as tris-(n-butyl)-phosphate (TNBP), or the like, and a surfactant such as Tween-80 or the like, exposing the protein formulations to particular chemical substances, such as an organic acid, for example, caprylic acid or the like, an alcohol having 4 to 10 carbon atoms, β-propiolactone, and the like, treatment of the protein formulation with a photosensitive compound such as psoralen, or the like, and ultraviolet irradiation treatment of the protein formulation with gamma irradiation, and so on (Sofer, et al. BioPharm International, Oct. 42-51, 2002).

However, the target proteins are at risk of being denatured or decomposed under the severe environmental conditions created by any of the above-mentioned inactivation methods. Furthermore, when an inactivating agent is added to the protein formulation, the inactivating agent must be separated and removed from the protein formulation after the inactivation step.

Certain viruses coated with a lipid envelope are known to drastically lose their infectivity simply by being exposed to an acidic pH at low temperatures for a short period of time (0.5 to one hour). In light of this, inactivating viruses using an acid treatment with an acid such as citric acid or the like has been introduced in the production process of various kinds of protein formulations (Brorson, et al. Biotechnology and Bioengineering 82, 321-329, 2003). The above-mentioned inactivation method is a remarkably simple process for virus inactivation. To be more specific, the protein solution is adjusted to pH 5 or less using a buffer solution which acts to adjust the pH, and the protein formulation is then maintained at a chosen temperature ranging from about 0 to about 30° C. for a short period of time, and the inactivation reaction proceeds. Once the formulation is neutralized using a base, the production process of the formulation can be reinitiated. In this case, virus inactivation is triggered merely by the acid pH treatment, so no further particular chemical substances are needed. Accordingly, the extra step of removing such chemical substances is not required. Although the acid sensitivity varies among viruses, previous reports have revealed that the exposure to acidic conditions greater than pH 3.5-4 is required to effectively inactivate the viruses (Sofer, et. al. BioPharm International, Apr. 42-68, 2003; Burstyn, et al. Developments in Biological Standardization 88, 73-79 (1996)). For example, Louie et al. demonstrated how to inactivate the bovine viral diarrhea virus (BVDV) by treating with acid, and consequently found that the BVDV cannot be completely inactivated even when subjected to a pH of 4.25 at a temperature of 21° C. for 21 days (Louie, et al. Biologicals 22, 13-19, 1994). Some protein formulations use more hardy proteins that do not denature or decompose even when exposed to strongly acidic pH conditions while other formulations use proteins such as antibodies which are prone to denaturation or association under strongly acidic conditions (Paborji, M. et al: Pharmaceutical Research. 11, 764-771 (1994)). Therefore, in order to assure the quality of the target proteins, due consideration must be given regarding the acid treatment of the proteins that may cause denaturation or association under the strongly acidic conditions. Thus, there is a demand for a virus inactivation method which uses more moderate acid treatment, for example, under slightly acidic pH conditions, and which is capable of inactivating the viruses similar to the methods using stronger acids.

Milton et al. found a method for inactivating viruses when preparing immunoglobulin formulations which combines treating with solvent/detergents and treating with an acid (EP0523406). This method is conducted at pH 4 to 4.85, and greatly improves the efficiency of viral inactivation when compared with conventional solvent/detergent methods. Although this combination method can result in more moderate pH conditions, it is necessary to remove the added organic solvent and surfactant. Juergen et al. found a method for preparing immunoglobulin formulations substantially free from viruses which employs the step of inactivating the viruses by exposing the protein formulation to caprylic acid or heptanoic acid at pH 4.6 to 4.95 (WO2005082937). Johnston et al. demonstrated that the titer of BVDV was decreased to $^{1}\!/_{10000}$ when the formulation was exposed to 16 mM caprylic acid at 30° C. for 10 hours and pH 4.5, and then proposed inactivating using an acid treatment and a chemical substance in combination (Biologicals 31, 213-221 (2003)). However, these methods still require the subsequent step of removing caprylic acid or the like, although more moderate pH conditions are achieved. In addition, it has been known for more than 40 years that the viruses in protein formulations can be effectively inactivated when a slight amount of pepsin is added to the protein formulation and adjusted to pH 4.0 (Jensch, et al. Transfusion 31, 423-427 (1991); Kempf, et al. Transfusion 36, 866-872 (1996)). Although more moderate pH conditions are possible in this method, the intentional addition of pepsin, for example, a protease, to the target protein is not considered to be an advantageous choice to ensure the quality of the target protein.

Arginine is known to inhibit nonspecific association and aggregation of proteins, and also is known to elute the protein from the column in purification and analysis using column chromatography (Tsumoto, et al Biotechnology Progress. 20, 1301-1308 (2004)).

SUMMARY OF THE INVENTION

An aspect of the present invention is to provide a method for conveniently producing a protein formulation in which the viruses are inactivated, without impairing the quality of the resulting protein formulation.

Another aspect of the present invention is to provide a method for conveniently inactivating the viruses present in a protein formulation, without impairing the quality of the protein formulation.

A further aspect of the present invention is to provide a method for conveniently inactivating viruses present on the surface of an article or material and the like.

The inventors of the present invention have intensively studied and have found that the above-mentioned aspects can be achieved by contacting a protein formulation with an arginine solution at a specific pH and concentration.

Namely, the present invention provides a method for producing a protein formulation in which viruses are inactivated comprising A) exposing the protein formulation contaminated with the viruses to an aqueous solution of arginine, an arginine derivative, or a mixture thereof in a concentration ranging from 0.1 to 2 M, and B) adjusting the pH of the aqueous solution to between 3.5 and 5.

The present invention further provides a method for inactivating viruses present in a protein formulation comprising A) exposing the protein formulation contaminated with the viruses to an aqueous solution of arginine, an arginine derivative, or a mixture thereof in a concentration ranging from 0.1 to 2 M, and B) adjusting the pH of the aqueous solution to between 3.5 and 5.

The present invention further provides a virus inactivation method comprising A) contacting a virus-containing object with an aqueous solution of arginine, an arginine derivative, or a mixture thereof in a concentration ranging from 0.1 to 2 M, and B) adjusting the pH of the aqueous solution to between 3.5 and 5.

According to the present invention, it is possible to produce protein formulations where viruses are highly inactivated with minimal steps. Arginine or derivatives thereof can be used as the pharmaceutical additives for protein formulations, so that it is not necessary to remove the arginine or derivatives thereof from the protein formulations since the qualities of the resulting protein formulations are not impaired. Furthermore, arginine or derivatives thereof can be used to purify the protein, since protein purification can be carried out concurrently with viral inactivation according to the present invention. The present invention also makes it possible to inactivate viruses present on the surfaces of solids such as articles or materials, human tissues, and tissues of other animals and plants, and the like. Furthermore, viruses present in liquids such as pharmaceutical drugs in the form of a solution, syrup and the like, liquid type foods such as refreshing drinks, mayonnaise and the like can be inactivated, as well as viruses present in gases such as air and the like, under moderate conditions in a short time, without having any adverse effect on the characteristics of the individual target object.

DETAILED DESCRIPTION OF THE PREFERRED EMBODIMENTS

The protein formulations of the present invention are made from organism-derived starting materials, cells, and/or animal-derived materials which are employed in the manufacturing process, so that viral inactivation is absolutely necessary. For example, the protein formulations include antibodies obtained from human plasma, humanized antibodies, human antibodies prepared by gene-engineered cell culture technology, mouse monoclonal antibodies, and the like. To be more specific, these protein formulations include Muramomab (product name: Orthclone OKT3), Rituximab (product name: Ritaxan), Basiliximab (product name: Simulect), Daclizumab (product name: Zenapax), Palivizumab (product name: Synagis), Infliximab (product name: Remicade), Gemtuzumab zogamicn (product name: Mylotarg), Alemtuzumab (product name: Mabcampath), Adalimumab (product name: Humira), Omalizumab (product name: Xolair), Vevacizumab (product name: Avastin), Cetuximab (product name: Erbitux), and the like. The present invention is especially useful in the preparation of the humanized and human antibodies, and can also be applied to the preparation of pharmaceutical formulations from human plasma-derived protein pharmaceuticals, vaccines, enzymes for therapeutic use, and the like. More specifically, the protein formulations include those made from donated blood plasma fractionation (eg. albumin, blood coagulation factor VII formulations, blood coagulation factor VIII formulations), influenza vaccines, thrombolytic agents (i.e., urokinase, tissue plasminogen activator), and the like.

Arginine and the derivatives thereof may be in the form of acid addition salts. Examples of acids capable of forming the acid addition salts include hydrochloric acid, sulfuric acid, and the like. Particularly preferred is hydrochloric acid. The arginine derivatives are not particularly limited. Arginine and derivatives thereof are preferable because they are suitable for purification of the protein formulations. Examples of the arginine derivatives include acylated arginines, such as Nα-acetyl-L-arginine, Nα-butyroyl-L-arginine, Nα-pivaloyl-L-arginine, Nα-valeroyl-L-arginine, Nα-caproyl-L-arginine, and the like, agmatine obtained from arginine by decarboxylation, arginic acid obtained by replacing the α-amino group by hydroxyl group, and the like. In particular, acylated arginines are preferable, such as Nα-acetyl-L-arginine, Nα-butyroyl-L-arginine, Nα-pivaloyl-L-arginine, Nα-valeroyl-L-arginine, and Nα-caproyl-L-arginine. Nα-butyroyl-L-arginine is most preferable.

The aqueous solution of arginine, the aqueous solution of an arginine derivative, or the mixture thereof is adjusted to have a concentration of 0.1 to 2 M, more preferably 0.15 to 2 M, and most preferably 0.2 to 1.0 M. When the concentration is 0.1 M or more, significant viral inactivation is achieved. The upper limit is set to be 2 M for economical reasons. The pH of such an arginine-containing solution at 25° C., which can be determined using glass electrodes, is in the range of pH 3.5 to 5, preferably pH 3.8 to 5, and most preferably pH 4 to 4.5. Preferably, inactivation of viruses can rapidly proceed within such a pH range. The pH of the arginine solution may be adjusted solely by the choice of the particular arginine or arginine derivatives. Alternatively, the pH of the solution can be adjusted by adding an acid such as hydrochloric acid or the like, or an alkali such as sodium hydroxide or the like. In order to more efficiently inactivate the viruses, a pH buffering ability may be imparted to the arginine solution by adding a dilute buffer solution such as acetate or phosphate in a concentration range of, for example, 5 to 50 mM.

During the manufacturing of protein formulations, contamination with viruses may occur, and any contaminating viruses can be inactivated by contacting or exposing the protein formulation with an arginine solution, an arginine derivative solution, or a mixture thereof which is adjusted to have a specific pH and concentration as specified above. Methods for how to contact or expose the virus-containing protein formulation with the arginine solution include maintaining the specified pH conditions even after the protein is subjected to purification by chromatography or directly adding the arginine to an aqueous solution containing the protein isolated from blood plasma or a cell culture supernatant to the desired arginine concentration and pH as specified above. When the protein is exposed to the arginine via the purification step using chromatography, the protein formulation may be, for example, dissolved in a phosphate buffer of a neutral pH or diluted about 10× with the buffer solution, and then introduced onto a column such as a protein A column (e.g., "HiTrap rProtein AFF, made by Amersham Bioscience K.K.) pre-equilibrated with the same buffer solution as mentioned above. After that, the column is thoroughly washed with the same buffer solution to rinse out the impurities derived from the raw materials. Then, an aqueous solution of arginine, an arginine derivative, or the mixture thereof with the desired pH is introduced onto the column. The desorbed protein formulation may then be collected. This process simultaneously inactivates any viruses and also purifies the protein formulation. The operating temperature may generally be in the range of 0 to 30° C., and preferably 0 to 8° C., in consideration of inactivation of the viruses, and at the same time, prevention of the protein from freezing and denaturing. The operating time may be generally in the range from about 15 minutes to about two hours, and preferably about one hour. Within the above-mentioned operating time, the viruses lose their infectivity and are finally inactivated by the action of arginine.

Also, viruses present on a target object can be inactivated effectively in a short time by contacting or exposing the object to an arginine solution, an arginine derivative solution, or the mixture thereof which is adjusted to have a particular pH and concentration as specified above. In this case, the aqueous solution of arginine, the aqueous solution of arginine derivative, or the mixture thereof is adjusted to have a concentration of 0.1 to 2 M, more preferably 0.1 to 1 M, and most preferably 0.1 to 0.3 M. The aqueous solution of arginine having the above-specified concentration is adjusted to pH 3.5 to 5, preferably pH 3.6 to 4.8, and more preferably pH 3.6 to 4.5 at 25° C. When the pH of the arginine-containing solution is lower than 3.5, the solution becomes more irritating to animal tissues, and therefore is not considered to be advantageous over the conventionally known methods, such as using citric acid. A pH of more than 5 is unfavorable because the virus inactivating effect decreases.

The target object is not particularly limited, but includes, for example, solids, liquids, and gases, so long as the object may be contaminated with viruses. Examples of a solid object include articles such as medical appliances, straps in trains and the like, furniture, household electric appliances, bedding such as a futon and the like, clothes, pets such as dogs, cats and the like, animal tissues, for example, the upper or lower part of respiratory tract, oral cavity and skin of human, and plant tissues, for example, the epidermis and the like. Examples of a liquid object include pharmaceutical preparations such as solutions, syrups and the like, liquids such as refreshing drinks and the like, and semi-solid foods such as mayonnaise and the like. The gaseous object includes air and the like.

The object contaminated with viruses may be brought into contact with an arginine-containing solution as described above by spraying the object using an atomizer, or coating the object using a brush or the like. Alternatively, an arginine-impregnated nonwoven fabric may be applied to the object or a portion thereof, or inserted into the inner side of a mask, or the like. When the arginine-containing solution is brought into contact with a liquid object, the arginine solution may be mixed or stirred with the liquid (object), if necessary. The means for mixing or stirring is not particularly limited. When the liquid (object) is an oleaginous substance such as an oil or fat, an emulsifier or the like may be added so that the liquid (object) and the aqueous solution may sufficiently come in contact with each other. Also, a polymer such as methyl cellulose or the like may be added to the above-mentioned arginine aqueous solution to impart the thickening effect to the aqueous solution. This can prolong the contact time of the liquid (object) with the arginine aqueous solution, thereby ensuring a sufficient time to inactivate the viruses in the liquid (object).

The surface temperature of the tissues of human and animals typically ranges from room temperature to body temperature. When the arginine-containing solution is applied to the tissues of animals, such as human tissues and the like, the inactivation reaction of the virus, for example, influenza virus, proceeds even more rapidly than when the viruses are exposed to the inactivating solution at low temperatures. In this case, the inactivation reaction is complete in about two minutes.

For example, when the influenza virus is attached to the upper respiratory tract of a human, the virus can be inactivated by a nasal spray of the above-mentioned arginine solution. Although the exposure time of the tissue surfaces of the upper respiratory tract to the arginine solution is short, the inactivation of the virus is achieved.

When the target object is brought into contact with the above-mentioned arginine solution, the amount of the arginine solution varies depending on the manner of contact. For example, when the above-mentioned aqueous solution of arginine is nasally sprayed on the human mucosa of the upper respiratory tract, the dosage of the aqueous solution is generally about 0.1 ml. The mucosa of the upper respiratory tract is exposed to the atomized aqueous arginine solution for several minutes after the spraying is complete, so that the influenza viruses is reliably inactivated even if they remain on the mucosa. Similarly, when the influenza viruses are attached to exposed tissues such as the palm, those viruses can be inactivated instantaneously by spraying about 0.1 ml of the above-mentioned aqueous arginine solution.

The amount of the aqueous solution to be sprayed may be properly determined depending upon the surface area of the target tissue. Also, when the influenza viruses are attached to the surface of appliances, for example, the viruses can be inactivated instantaneously by spraying the above-mentioned aqueous solution on the surface of the target appliance at room temperature or above, in a proper amount depending upon the surface area of the target object.

The kinds of viruses to be inactivated are not particularly limited. For example, influenza virus, rhinovirus, and coronavirus can be mentioned. The present invention is particularly effective in inactivating lipid-enveloped viruses.

To evaluate the inactivating efficiency, a concentrated virus stock with an identified viral titer is first added to a protein solution. After exposure to the inactivating solution, the residual virus titer is determined by any suitable method, such as $TCID_{50}$, plaque assay, and the like. The log reduction value (LRV) is defined as the common logarithm ($\log_{10}$) of the ratio of the virus load in a sample before inactivation to the virus content in the sample after inactivation. This value is calculated, and the calculated LRV is determinative of the inactivating efficiency. The inactivating efficiency is considered to be significant when the LRV is 1 or more (ICH Harmonized Tripartite Guideline: Viral Safety Evaluation of Biotechnology Products Derived from Cell Lines of Human or Animal Origin).

When the protein formulations obtained by the method of the present invention are analyzed by gel filtration chromatography, the proteins elute with the same peaks appearing at the same retention time as when the proteins are in their native state. Therefore, the protein formulations have not been subjected to changes in high-order structure, association, or aggregation.

The protein formulations obtained by the method of the present invention can be used to produce therapeutic agents, reagents for clinical laboratory tests, and laboratory-grade reagents for various diseases such as cancer, immune system disorders, lifestyle-related diseases, and the like. The pharmaceutical compositions may further include appropriate excipients, carriers and the like, in addition to the purified antibodies obtained by the method of the present invention.

Furthermore, the present invention is also applicable to producing inactivating agents capable of inactivating viruses such as influenza virus, rhinovirus, coronavirus, and the like, and inhibitors of viral infectious diseases related to the above-mentioned viruses. These inactivating agents and inhibitors may also include pharmaceutically acceptable excipients, carriers and the like, and may be prepared in the liquid form or the like by conventional methods.

Example 1

30 mL of a solution was prepared by dissolving purified anti-von Willebrand Factor monoclonal antibody (mouse monoclonal antibody, subclass $IgG_1$; WO96/17078) in Dulbecco's isotonic phosphate buffer solution (free from Ca and Mg). After having divided the solution in half, each aliquot (15 ml) of the solution was subjected to overnight dialysis against 5000 ml of 5 mM sodium phosphate (pH 4.4). This dialysis was conducted twice, respectively. The dialyzed antibody fluids (inner part) were combined to yield about 30 ml. The solution thus obtained was then adjusted to have an antibody concentration of 10 mg/ml using the outer part of the dialysis. The concentration-adjusted solution (5 ml) was diluted twice with each of the buffer solutions for virus inactivation which were separately prepared, and thereafter finely adjusted to have a predetermined pH value using 2M NaOH or 2M aqueous solution of hydrochloric acid. Each of the obtained solutions was subjected to sterile filtration using a disposable filter (0.22 μm) and stored at 5° C. Table 1 shows the inactivating conditions for each buffer solution.

Using the Vero cell, the herpes simplex viruses type 1, strain F (HSV-1) was grown in an Eagle's minimum essential medium (MEM) containing 0.5% fetal calf serum, thereby preparing a concentrated virus suspension. This virus-containing suspension was stored at −80° C. The viral titer was determined using the Vero cell in accordance with the plaque assay known from the previous report (Koyama, et. al. Virus Res. 13, 271-282 (1989)). While on ice, 0.95 ml of each of the virus-inactivating buffer solutions shown in Table 1 was put into a 1.5-ml plastic tube, where 0.05 ml of the concentrated HSV-1 suspension (with a virus concentration of about $10^9$ plaque forming units (PFU)/ml) was further added. After the mixture was instantaneously stirred, the mixture was kept on ice for one hour. After that, the mixture was diluted 100 times with Dulbecco's isotonic phosphate buffer solution (free from Ca and Mg) containing 1% fetal calf serum to conduct pH neutralization titration, thereby terminating the virus inactivating reaction. The reaction solution was appropriately diluted with Dulbecco's isotonic phosphate buffer solution (free from Ca and Mg) containing 1% fetal calf serum, and the residual HSV-1 titer (the concentration of the viruses still remaining infectious) was determined using the plaque assay previously mentioned. In accordance with the ICH Harmonized Tripartite Guideline mentioned above, the titer of HSV-1 loaded in a sample was determined after the sample had been on ice for one hour in a Dulbecco's isotonic phosphate buffer solution instead of the virus inactivating buffer solution. The titer of HSV-1 thus obtained after completion of the holding time was regarded as a virus load in the sample before inactivation. The virus inactivating efficiency was defined as the $log_{10}$ of the ratio of the virus load before inactivation to that after inactivation (Table 1).

As shown in Table 1, the inactivation did not take place when the 0.1 M citrate buffer solution of pH 4.3 was employed. Even when the citrate buffer solution adjusted to pH 4.0 was employed, the degree of inactivation was considerably slight (LRV=1.5). The inactivation effect was sharply increased (LRV>5.7) at pH 3.5. These results are in agreement with the findings from the prior art. Namely, to inactivate the viruses using sodium citrate, the acidic conditions corresponding to pH<4 are necessary. On the other hand, any of the buffer solutions of 1M arginine hydrochloride (pH 4.3), 0.7 M arginine hydrochloride (pH 4.0), and 0.7 M Nα-butyroyl-L-arginine (pH 4.0) showed the same level of the inactivation effect as with the sodium citrate at pH 3.5.

As mentioned above, arginine and acyl arginine are found to have a strong inactivation effect on the HSV-1 under moderately acidic conditions of around pH 4.

TABLE 1

| Inactivating Conditions | | Virus Inactivating |
| --- | --- | --- |
| Buffer solution composition | pH | Efficiency (LRV) |
| Dulbecco's isotonic phosphate buffer solution | 7.2 | — |
| 0.1M sodium citrate | 4.3 | 0.1 |
| 0.1M sodium citrate | 4.0 | 1.5 |
| 0.1M sodium citrate | 3.5 | >5.7 |
| 1M arginine hydrochloride | 4.3 | >5.7 |
| 0.7M arginine hydrochloride, 20 mM sodium acetate | 4.0 | >5.7 |
| 0.7M Nα-butyroyl-L-arginine | 4.0 | >5.7 |

LRV = $log_{10}$ (virus load/residual virus content)
Virus load: concentration of viruses in the sample retained in Dulbecco's isotonic phosphate buffer solution.
Residual virus content: concentration of viruses still remaining in the sample subjected to inactivation.

Example 2

Using MDCK cells, the Influenza A viruses/Aichi were grown in an Eagle's minimum essential medium (MEM) containing 0.1% bovine serum albumin and 4 μg/ml acetylated trypsin, thereby preparing a concentrated virus suspension. This virus suspension was stored at −80° C. The viral titer was determined using the MDCK cells in accordance with the plaque assay known from the previous report (Kurokawa et. al.: Intern. J. Mol. Med. 3, 527-530 (1999)). While on ice, 0.95 ml of each of the same virus-inactivating buffer solutions as employed in Example 1 was put into a 1.5-ml plastic tube, where 0.05 ml of the concentrated influenza A virus suspension (with a virus titer of about $10^8$ PFU/ml) was further added. After the mixture was instantaneously stirred, the mixture was kept on ice for one hour. After that, the mixture was diluted 100 times with Dulbecco's isotonic phosphate buffer solution (free from Ca and Mg) containing 0.1% bovine serum albumin to conduct pH neutralization titration, thereby terminating the virus inactivating reaction. The reaction solution was appropriately diluted with Dulbecco's isotonic phosphate buffer solution (free from Ca and Mg) containing 0.1% bovine serum albumin and the residual influenza A virus titer (the titer of the viruses still remaining infectious) was determined using the plaque assay previously mentioned. In accordance with the ICH Harmonized Tripartite Guideline mentioned above, the titer of influenza A virus loaded in a sample was determined after the sample had been on ice for one hour in a Dulbecco's isotonic phosphate buffer solution (free from Ca and Mg) instead of the virus inactivating buffer solution. The titer of influenza A virus thus obtained after completion of the retention time was regarded as a virus load in the sample before inactivation. The virus inactivating efficiency was defined as the $\log_{10}$ of the ratio of the virus load before inactivation to that after inactivation (Table 2).

As shown in Table 2, the virus was inactivated by a 0.1 M citrate buffer solution at pH 4.3 although the inactivating level was slight (LRV=1.3). This attests to the fact that the surface antigen Hemagglutinin (HA) is unstable under acidic conditions. However, any change in the inactivating efficiency was hardly observed (LRV=1.5) at a more acidic value of pH 4.0; and the inactivation level was still slight (LRV=2.1) even though the citrate buffer solution was adjusted to pH 3.5. On the other hand, the inactivating effect (LRV=2.4) obtained by the buffer solution of 1M arginine hydrochloride of pH 4.3 was found to be higher than that of the sodium citrate of pH 3.5. Furthermore, 0.7 M arginine hydrochloride (pH 4.0) and 0.7 M Nα-butyroyl-L-arginine (pH 4.0) showed even more inactivating power to achieve the LRV of 3.7.

As mentioned above, arginine and acyl arginine are also found to have strong effects in inactivating the influenza A virus under moderately acidic conditions of around pH 4.

TABLE 2

| Inactivating Conditions | | Virus Inactivating |
|---|---|---|
| Buffer solution composition | pH | Efficiency (LRV) |
| Dulbecco's isotonic phosphate buffer solution | 7.2 | — |
| 0.1M sodium citrate | 4.3 | 1.3 |
| 0.1M sodium citrate | 4.0 | 1.5 |
| 0.1M sodium citrate | 3.5 | 2.1 |
| 1M arginine hydrochloride | 4.3 | 2.4 |
| 0.7M arginine hydrochloride, 20 mM sodium acetate | 4.0 | 3.7 |
| 0.7M Nα-butyroyl-L-arginine | 4.0 | 3.7 |

LRV = $\log_{10}$ (virus load/residual virus content)
Virus load: concentration of viruses in the sample retained in Dulbecco's isotonic phosphate buffer solution.
Residual virus content: concentration of viruses still remaining in the sample subjected to inactivation.

Example 3

Using the HSV-1 suspension prepared in the same manner as in Example 1, the relationship between the virus inactivating effect and the salt concentration was investigated. The viral titer was determined in accordance with the plaque assay in the same manner as in Example 1. As shown in Table 3, the buffer solutions of 1 M NaCl (pH 4.3) and 0.7 M NaCl (pH 4.0) were found to have extremely weak inactivating effects (LRV=0.8 at most) unlike the buffer solutions of arginine and Nα-butyroyl-L-arginine, although the respective concentrations of those NaCl buffer solutions were the same as those of the arginine hydrochloride and Nα-butyroyl-L-arginine which exhibited sufficient inactivating effects in Examples 1 and 2. On the other hand, when the concentration of the arginine hydrochloride (pH 4.0) was changed to 0.35 M, the inactivating effect became slightly less, but the level was still sufficient (LRV=4.2). The buffer solution of 0.35 M Nα-butyroyl-L-arginine (pH 4.0) showed an extremely strong inactivating effect (LRV>5.5).

The above-mentioned findings demonstrate that the inactivating effects of arginine and acyl arginine are not just attributed to the salt concentration, but based on properties specific to arginine. When the buffer solutions of 0.1 M arginine hydrochloride and 0.7 M arginine hydrochloride were adjusted to pH 3.5, their respective inactivating effects exhibited the same levels as that of the 0.1 M sodium citrate (pH 3.5) as expected.

TABLE 3

| Inactivating Conditions | | Virus Inactivating |
|---|---|---|
| Buffer solution composition | pH | Efficiency (LRV) |
| Dulbecco's isotonic phosphate buffer solution | 7.2 | — |
| 1M NaCl, 0.02M sodium acetate | 4.3 | 0 |
| 0.7M NaCl, 0.02M sodium acetate | 4.0 | 0.8 |
| 0.35M arginine hydrochloride | 4.0 | 4.2 |
| 0.35M Nα-butyroyl-L-arginine | 4.0 | >5.5 |
| 0.7M arginine hydrochloride | 3.5 | >5.5 |
| 0.1M arginine hydrochloride | 3.5 | >5.5 |

LRV = $\log_{10}$ (virus load/residual virus content)
Virus load: concentration of viruses in the sample retained in Dulbecco's isotonic phosphate buffer solution.
Residual virus content: concentration of viruses still remaining in the sample subjected to inactivation.

Example 4

Using the concentrated HSV-1 suspension prepared in the same manner as in Example 1, the relationship between the virus inactivating effect and the concentrations of arginine or acyl arginine was investigated (Table 4). The viral titer was determined in accordance with the plaque assay in the same manner as in Example 1. As shown in Table 4, when the concentration was 0.14 M or more, both the arginine hydrochloride and the Nα-butyroyl-L-arginine showed significant inactivating effects (LRV>1.0). When the arginine hydrochloride was compared with the Nα-butyroyl-L-arginine, for example, at a concentration of 0.28 M, the inactivating effect of the latter appeared to be significantly stronger than that of the former.

TABLE 4

| | Virus Inactivating Efficiency (LRV) | |
|---|---|---|
| Concentration (M) | Arginine hydrochloride (pH 4.0) | Nα-butyroyl-L-arginine (pH 4.0) |
| 0 | — | — |
| 0.07 | 0.5 | 0.7 |
| 0.14 | 1.1 | 2.2 |
| 0.21 | 2.2 | 4.3 |
| 0.28 | 3.1 | 6.0 |
| 0.35 | 4.5 | not determined |

LRV = $\log_{10}$ (virus load/residual virus content)
Virus load: concentration of viruses in the sample retained in Dulbecco's isotonic phosphate buffer solution.
Residual virus content: concentration of viruses still remaining in the sample subjected to inactivation.

Example 5

Sendai viruses were cultured using embryonated egg, and then a virus-containing suspension was prepared by appropriately diluting with Dulbecco's isotonic phosphate buffer solution (free from Ca and Mg) containing 0.1% bovine serum albumin. This virus suspension was stored at −80° C. The viral titer was determined by the plaque assay in the same manner as in Example 2 except that the MDCK cell was replaced by the Vero cell. While on ice, 0.95 ml of each of the virus-inactivating buffer solutions, i.e., 0.1M sodium citrate (pH 3.5), 0.7M NaCl (pH 4.0) and 0.7M Nα-butyroyl-L-arginine (pH 4.0) was put into a 1.5-ml plastic tube, where 0.05 ml of the concentrated Sendai virus suspension (with a virus titer of about $10^8$ to $10^9$ PFU/ml) was further added. The mixture was instantaneously stirred, and then kept on ice for one hour. As control samples for reference, an isotonic phosphate buffer solution (pH 7.2) and a strongly acidic isotonic citrate buffer solution (pH 3.0) known to have an extremely powerful inactivating effect were used. After completion of the retention time, the reaction mixture was diluted 100 times with Dulbecco's isotonic phosphate buffer solution (free from Ca and Mg) containing 0.1% bovine serum albumin to conduct pH neutralization titration, thereby terminating the virus inactivating reaction. The reaction solution was appropriately diluted with Dulbecco's isotonic phosphate buffer solution (free from Ca and Mg) containing 0.1% bovine serum albumin and the residual Sendai virus titer (the titer of the viruses still remaining infectious) was determined using the plaque assay previously mentioned. The titer of the Sendai virus loaded in a sample was determined after the sample had been retained for one hour in a Dulbecco's isotonic phosphate buffer solution (free from Ca and Mg) instead of the virus inactivating buffer solution. This was regarded as a virus load in the sample before inactivation. The virus inactivating efficiency was defined as the $\log_{10}$ of the ratio of the virus load before inactivation to that after inactivation (Table 5).

As is apparent from Table 5, both the buffer solutions of 0.1M sodium citrate (pH 3.5) and 0.7M NaCl (pH 4.0) had no inactivating effect, while the buffer solution of 0.7M Nα-butyroyl-L-arginine (pH 4.0) exhibited the inactivating effect (LRV>3.7) higher than that of the isotonic citrate buffer solution (40 mM sodium citrate, 5.0 mM KCl, 125 mM NaCl, Ph 3.0; Microbiol. Immunol., 31, 123-130 (1987)) which is a strongly acidic solution capable of creating powerful inactivating conditions.

In addition to the results of Example 4, the following demonstrate that the arginine derivative has considerably powerful effects in inactivating the viruses.

TABLE 5

| Inactivating Conditions | | Virus Inactivating |
|---|---|---|
| Buffer solution composition | pH | Efficiency (LRV) |
| Dulbecco's isotonic phosphate buffer solution | 7.2 | — |
| Isotonic citrate buffer solution(*) | 3.0 | 3.4 |
| 0.1M sodium citrate | 3.5 | 0.3 |
| 0.7M NaCl, 0.02M sodium acetate | 4.0 | 0.1 |
| 0.7M Nα-butyroyl-L-arginine | 4.0 | >3.7 |

LRV = $\log_{10}$ (virus load/residual virus content)
Virus load: concentration of viruses in the sample retained in Dulbecco's isotonic phosphate buffer solution.
Residual virus content: concentration of viruses still remaining in the sample subjected to inactivation.
Isotonic citrate buffer solution (*): 40 mM sodium citrate, 5.0 mM KCl, 125 mM NaCl, pH 3.0.

Example 6

Using the influenza virus A/Aichi (H3N2) suspension prepared in the same manner as in Example 2, the relationship of the virus inactivating effect to the composition of the inactivating buffer solution and the pH thereof was investigated. The concentration of each buffer solution was set to 0.15M, the inactivating temperature was raised to a room temperature of 21.6° C., and the inactivating time was shortened to two minutes. A 2.2-ml plastic tube equipped with a screw cap was charged with 190 μl of each of the inactivating buffer solutions shown in Table 6 and stored on ice. To each of the buffer solutions, which had been separately prepared by the addition of bovine serum albumin serving as a carrier protein in a concentration of 5 mg/ml, 10 μl of the influenza virus A suspension (with a virus concentration of about $10^8$ PFU/ml) was further added. After the mixture was instantaneously stirred, the mixture was placed in a thermostatic chamber of 21.6° C. for two minutes. Two minutes later, each sample was immediately cooled using ice water, and subsequently diluted 100 times with Dulbecco's isotonic phosphate buffer solution (free from Ca and Mg) containing 0.1% bovine serum albumin to conduct pH neutralization titration, thereby terminating the virus inactivating reaction. The residual virus titer was determined using the plaque assay in the same manner as in Example 2. The titer of the influenza virus A loaded in a sample was determined after the sample had been retained in a Dulbecco's isotonic phosphate buffer solution (free from Ca and Mg) instead of the virus inactivating buffer solution at 21.6° C. for two minutes. This titer of the influenza virus A was regarded as a virus load in the sample before inactivation. The virus inactivating efficiency was defined as the $\log_{10}$ of the ratio of the virus load in the sample before inactivation to that after inactivation (Table 6).

As shown in Table 6, when the pH value was set to 3.8, buffer solutions of 0.15M PCA (pyrrolidone carboxylic acid), 0.15M arginine hydrochloride, and 0.15M Nα-butyroyl-L-arginine showed high LRV values of more than 4.35 and they were found to have powerful inactivating effects. In the case of the 0.15M sodium citrate, the maximum LRV was 2.95 at most within the pH range of 3.8 to 4.2. Namely, the 0.15M sodium citrate appeared to function less than the other three kinds of buffer solutions in the virus inactivation. When the pH value was raised to 4.2, the arginine hydrochloride and the Nα-butyroyl-L-arginine still maintained high LRV values of more than 3.0, although the inactivating effects were somewhat lowered in any of PCA, arginine hydrochloride and Nα-butyroyl-L-arginine.

As previously described, it has been confirmed that the influenza virus can be inactivated effectively by exposing the viruses to arginine hydrochloride or Nα-butyroyl-L-arginine at room temperature even for a short period of time, e.g., about two minutes. Those buffer solutions exhibited superior inactivating effects when compared with the sodium citrate and PCA at the same concentration.

TABLE 6

| Inactivating Conditions | | Virus Inactivating |
|---|---|---|
| Buffer solution composition | pH | Efficiency (LRV) |
| Dulbecco's isotonic phosphate buffer solution | 7.2 | — |
| 0.15M sodium citrate | 3.8 | 2.74 |
| 0.15M sodium citrate | 4.0 | 2.66 |
| 0.15M sodium citrate | 4.2 | 2.95 |
| 0.15M PCA | 3.8 | >4.35 |
| 0.15M PCA | 4.0 | 4.05 |
| 0.15M PCA | 4.2 | 2.95 |
| 0.15M arginine hydrochloride | 3.8 | >4.35 |
| 0.15M arginine hydrochloride | 4.0 | 3.87 |
| 0.15M arginine hydrochloride | 4.2 | 3.24 |
| 0.15M Nα-butyroyl-L-arginine | 3.8 | >4.35 |
| 0.15M Nα-butyroyl-L-arginine | 4.0 | 4.05 |
| 0.15M Nα-butyroyl-L-arginine | 4.2 | 3.57 |

LRV = $\log_{10}$ (virus load/residual virus content)
Virus load: concentration of viruses in the sample retained in Dulbecco's isotonic phosphate buffer solution.
Residual virus content: concentration of viruses still remaining in the sample subjected to inactivation.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing a protein formulation in which lipid-enveloped viruses are inactivated, comprising:
   A) preparing an aqueous solution containing 0.1 to 2 M of arginine, an arginine derivative, or a mixture thereof, and
   B) exposing a protein formulation contaminated with one or more lipid-enveloped viruses to an amount of the aqueous solution sufficient to inactivate the lipid-enveloped viruses, wherein the pH of the resultant solution is in the range of between 4 and 4.5.

2. The method of claim 1, wherein the arginine derivative is an acylated arginine.

3. The method of claim 2, wherein the acylated arginine is selected from the group consisting of Nα-acetyl-L-arginine, Nα-butyroyl-L-arginine, Nα-pivaloyl-L-arginine, Nα-valeroyl-L-arginine, and Nα-caproyl-L-arginine.

4. The method of claim 1, wherein the concentration of the arginine or the arginine derivative in the aqueous solution is 0.15 to 2 M.

5. The method of claim 1, wherein the protein formulation comprises a humanized antibody or a human antibody.

6. A method for inactivating lipid-enveloped viruses on the surface of a solid object comprising:
   A) preparing an aqueous solution comprising 0.1 to 2 M of arginine, an arginine derivative, or a mixture thereof, wherein the pH of the solution is in the range of between 4 and 5, and
   B) contacting a virus contaminated solid object with an amount of the aqueous solution sufficient to inactivate the lipid-enveloped viruses by a method selected from the group consisting of spraying the virus contaminated solid object with the aqueous solution, coating the virus contaminated solid object with the aqueous solution, and combination thereof.

7. The method of claim 6, wherein the solid object is selected from the group consisting of an article, animal tissue, and plant tissue.

8. The method of claim 6, wherein the arginine derivative is an acylated arginine.

9. The method of claim 8, wherein the acylated arginine is selected from the group consisting of Nα-acetyl-L-arginine, Nα-butyroyl-L-arginine, Nα-pivaloyl-L-arginine, Nα-valeroyl-L-arginine, and Nα-caproyl-L-arginine.

10. The method of claim 6, wherein the concentration of the arginine or the arginine derivative in the aqueous solution is 0.15 to 2M.

* * * * *

UNITED STATES PATENT AND TRADEMARK OFFICE
CERTIFICATE OF CORRECTION

PATENT NO. : 8,669,045 B2  
APPLICATION NO. : 12/030321  
DATED : March 11, 2014  
INVENTOR(S) : Hajime Koyama et al.

It is certified that error appears in the above-identified patent and that said Letters Patent is hereby corrected as shown below:

On the title page under item (57) abstract "10 Claims, No Drawings" should read -- 11 Claims, No Drawings --

In the Claims

Column 14, line 24, insert the following:
-- 11. A method for inactivating lipid-enveloped viruses present in a protein formulation comprising:
  A) preparing an aqueous solution comprising 0.1 to 2 M of arginine, an arginine derivative, or a mixture thereof, and
  B) exposing a protein formulation contaminated with one or more lipid-enveloped viruses to an amount of the aqueous solution sufficient to inactivate the lipid-enveloped viruses, wherein the pH of the resultant solution is in the range of between 4 and 4.5. --

Signed and Sealed this  
Seventeenth Day of June, 2014

Michelle K. Lee  
*Deputy Director of the United States Patent and Trademark Office*